United States Patent [19]
Koso

[11] Patent Number: 4,783,826
[45] Date of Patent: Nov. 8, 1988

[54] PATTERN INSPECTION SYSTEM

[75] Inventor: Dusan A. Koso, Cambridge, Mass.

[73] Assignee: The Gerber Scientific Company, Inc., South Windsor, Conn.

[21] Appl. No.: 897,721

[22] Filed: Aug. 18, 1986

[51] Int. Cl.⁴ .............................................. G06K 9/00
[52] U.S. Cl. ......................................... 382/8; 382/19; 358/101; 358/106
[58] Field of Search ..................... 382/8, 26, 19, 45; 358/101, 106, 107

[56] References Cited

U.S. PATENT DOCUMENTS

| | | | |
|---|---|---|---|
| 4,532,650 | 7/1985 | Wihl et al. | 358/101 |
| 4,623,256 | 11/1986 | Ikenaga et al. | 382/8 |
| 4,668,982 | 5/1987 | Tinnerino | 382/8 |
| 4,680,627 | 7/1987 | Sase et al. | 382/8 |

Primary Examiner—John W. Shepperd
Assistant Examiner—Michael D. Parker
Attorney, Agent, or Firm—Joseph S. Iandiorio; Douglas E. Denninger

[57] ABSTRACT

A system which inspects pattern-bearing material that is subject to topical distortions which scans in a first direction a plurality of predefined local regions of a pattern to be inspected to provide an image of each local region and generates a reference image for each of the local regions. The system shifts the position of the image of each local region and the position of its corresponding reference image relative to each other to align the images in the second direction and/or modifies in the first direction the dimension of the image of each local region and the dimension of its corresponding reference image relative to each other to align the images in the first direction. For each local region the system compares the aligned images to detect errors in the pattern independent of misalignment of and topical distortions of each local region.

31 Claims, 5 Drawing Sheets

PATTERN INSPECTION SYSTEM

FIELD OF INVENTION

This invention relates to a pattern inspection system which compensates for topical distortions and more particularly to such a system which rapidly detects layout errors in printed wire boards.

BACKGROUND OF INVENTION

Some image-bearing materials are subjected to further manufacturing processes after a pattern is applied to the material. These additional processes can create topical—regional—distortions in the material such that the material and thus the pattern varies nonuniformly across the length and breadth of the material. Some such materials are fabrics and printed wire boards. Difficulties arise when the quality of the patterns must be assured.

Presently, printed wire boards are inspected using time-consuming and expensive processes. Most of the inspection is performed manually; this method can amount to thirty to forty percent of the entire cost of the board.

The most common automatic inspection systems utilize the design rule approach. Under this approach, the inspection system examines a small area of the board to determine if the circuit fit certain design rules. For example, acceptable lines have a given uniform width, have a right-angle bend, or end in a pad. Errors are identified when a pattern does not match the rules: a line ending without a pad is an error, indicating that an open circuit exists; a line ending in a line is an error, indicating a short circuit. As designs increase in complexity, more rules are required to accurately describe acceptable circuits and computational demands increase. State of the art printed wire boards require a great deal of time for inspection by conventional design rule systems. Further, a change in design often necessitates alteration of the design rules.

Under another automatic inspection system, the golden board approach, a perfect or "golden" board is used as the standard to which production printed wire boards are compared. The golden board may be compared in its hardware embodiment or in the form of a data base, that is, a computer map of the golden board. The major problem with the golden board approach is that production printed wire boards typically exhibit shrinking or stretching distortions imparted by the manufacturing process which are nonuniform over the length of the production board. Circuit material typically varies in length and width 0.0005 inch per inch or up to 0.01 inch over 24 inches. While rarely rendering a production board defective, these topical distortions often prevent direct area-to-area matching between entire full-sized boards.

Further, complex boards can exert memory demands of nearly two gigabits to conventionally represent an entire printed wire board in a data base. The time required simply to retrieve and manipulate this vast quantity of information to accommodate the particular variations of a given board renders conventional golden board systems too slow to be economically feasible.

SUMMARY OF INVENTION

It is therefore an object of this invention to provide an improved inspection system for material which varies nonuniformly along its length and its width.

It is a further object of this invention to provide such a system which accurately aligns regions of the material with corresponding reference images.

It is a further object of this invention to provide an improved optical inspection system for printed wire boards.

It is a further object of this invention to provide such a system which does not generate false error indications when allowable localized stretching and shrinking occurs in the wire board.

It is a further object of this invention to provide such a system which accurately detects actual pattern errors.

It is a further object of this invention to provide such a system which is accurate and effective without using design rules.

It is a further object of this invention to provide such a system which can manipulate small portions of a reference data base outside its memory rather than manipulate the entire data base within memory.

This invention results from the realization that a truly effective system for inspecting printed wire boards can be achieved by defining a number of local regions within the printed wire board, generating a reference image for each region, and viewing each region with a camera to provide an image for that region. These images are compared to determine misalignment between each local region and its corresponding reference image, to align each local region with its corresponding reference image, and to detect actual pattern errors within each aligned local region.

This invention features a system which inspects a pattern-bearing material that is subject to topical distortions. There are means for scanning in a first direction a plurality of predefined local regions of a pattern to be inspected to provide an image of each local region. There are also means for generating a reference image for each of the local regions, means for shifting the position of the image of each local region and the position of its corresponding reference image relative to each other to align the images as a pair in the second direction, and means for modifying in the first direction the dimension of the image of each local region and the dimension of its corresponding reference image relative to each other to align the images as a pair in the first direction. There are means for comparing each pair of aligned images to detect errors in the pattern independent of misalignment of and topical distortions of each local region.

In one embodiment, the means for scanning includes camera means for producing the image of each local region. The means for shifting may include means for selecting within the scan width the field of view of the camera means utilized to produce the image and means for determining for each local region and its corresponding reference image the difference in position of the local region and the position of the reference image relative to each other in the second direction. The camera means may include a plurality of photosensitive elements such as a charge-coupled device.

The means for modifying may include means for representing for each local region and its corresponding reference image the difference in dimension of the local region relative to the dimension of the reference image in the first direction. The means for modifying may further include means for adjusting the dimension of the reference image in the first direction: the means for scanning provides the image of each local region as a first set of successive portions and the means for generating generates its corresponding reference image as a second set of successive portions and the means for adjusting repeats a portion of the reference image when the local region is shorter in the first direction than the reference image and deletes a portion of the reference image when the local region is longer in the first direction. Each portion can be a plurality of units and the means for comparing compares each local region unit to its corresponding reference image unit; each unit is at least as large in dimension as the maximum expected topical distortion in the pattern of each local region. The means for generating may generate the reference image for each local region as a set of successive lines and the means for adjusting, for a reference image having N lines, repeats line N−1 of the reference image when the local region is shorter in the first direction than the reference image and jumps from line N−1 to the first line of the next reference image when the local region is longer in the first direction. The reference images can be arranged sequentially in the first direction.

In a preferred embodiment, the means for generating generates digital reference images and includes memory means for storing the reference images in digital form; the means for scanning provides digital images of the local areas and the means for comparing includes digital comparison means. The pattern is disposed on a printed wire board and the second direction is transverse to the first direction along the plane of the pattern. The means for shifting and the means for modifying completely align each local region with its corresponding reference image in the first and second directions. The means for scanning further includes movable platform means and means for securing the pattern to the platform means. There is also means for coarsely aligning in the first direction the platform means and the camera means.

This invention also features a method of inspecting pattern-bearing material including defining a plurality of local regions in a pattern to be inspected, scanning the pattern by passing in a first direction the local regions to provide an image of each local region whereby the width of the scan in a second direction is greater than the width in the second direction of each local region. The method further includes generating, for each local region, a reference image corresponding to that local region, determining for each set of corresponding images the difference in position of the local region and the position of its corresponding reference image relative to each other in a second direction, and shifting the position of the image of each local region in a second direction relative to the position of its corresponding reference image to align the images in the second direction. For each local region, the aligned images are compared to detect errors in the pattern independent of misalignment of and topical distortions of each local region.

Shifting to align the images may include selecting within the scan width the field of view for each image to be produced. The step of determining may include initially scanning the pattern to view a portion of each region to resolve any offset in the second direction and the step of scanning to provide an image includes subsequently scanning each region by the field of view selected to compensate for the offset for that region.

This invention further features an inspection method including defining a plurality of local regions in a pattern to be inspected, scanning the pattern by passing in a first direction the local regions to provide an image of each local region and generating, for each local region, a reference image corresponding to that local region. The method further includes representing for each set of corresponding images the difference in dimension of the local region and the dimension of its reference image relative to each other in the first direction, modifying in the first direction the dimension of the image of each local region and the dimension of its corresponding reference image relative to each other to align the images in the first direction and comparing, for each local region, the aligned images to detect errors in the pattern.

The images may be provided as sets of successive portions and the dimension of the image of each local region may be modified relative to the dimension of its corresponding reference image by repeating or deleting a portion of the reference image. The step of representing may include initially scanning the pattern to view a portion of each region to resolve any offset in the first direction and the step of modifying includes altering the dimension of the corresponding reference image by that offset.

DISCLOSURE OF PREFERRED EMBODIMENTS

Other objects, features and advantages will occur from the following description of preferred embodiments and the accompanying drawings, in which.

Figure 1:
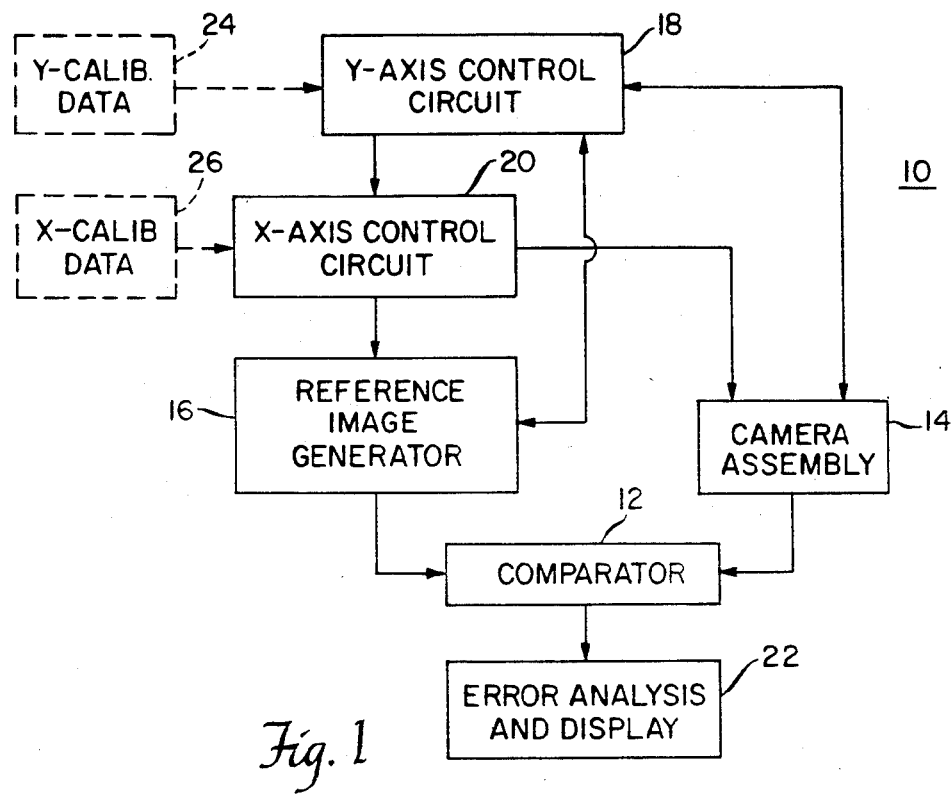
FIG. 1 is a schematic block diagram of a pattern inspection system according to this invention which provides alignment along both the X- and Y-axes of the material to be inspected with the reference image.

This invention for examining pattern-bearing material that varies nonuniformly may be accomplished by an inspection system which scans in a first direction the material in a number of predefined local regions to produce an image of each region, generates a corresponding reference image for each local region, and compares each pair of corresponding images to detect errors in each local region. Before comparing the pairs of images to detect errors, the inspection system aligns the images within each pair either in the first direction, in a second direction, or in both directions to avoid any possibility of false errors due to localized distortions rather than to actual defects in the pattern.

In one construction, a portion of each region is initially scanned by a camera to determine its actual X-Y location relative to its expected X-Y location; the expected X-Y location corresponds with the X-Y orientation of a reference image for that region. Any offset in the X-direction, that is, the direction normal to the direction of scanning, is compensated for by selecting a different field of view of the camera. The pattern is subsequently scanned by the selected field of view to provide the image of each region properly aligned in the X-direction. Information about any offset in the Y-direction is utilized to align the reference image with the image produced during the subsequent scan.

More generally, alignment in the first direction is accomplished by modifying the dimension of the image of each local region and the dimension of the corresponding reference image relative to each other. Preferably, the reference images are arranged sequentially; the dimension of each reference image must be modified so that misalignment between one pair of images, produced by a topical distortion, is not introduced to the next pair of images. That is, although images of a pair are aligned initially before comparison and remain aligned over most of their respective lengths in the first direction during comparison, the last portion of the reference image will not correspond with the last portion of the local region if there is a topical distortion in that local region. For example, when the topical distortion is a shrinkage along the first direction of the pattern in the local area, the corresponding reference image should be reduced in dimension to match the shorter length of that local area. The matching ensures that, for the next pair of images, the first portion of the local region is compared to the first portion of its corresponding reference image, i.e., that the next pair of images are aligned before comparison begins.

In one application, the pattern-bearing material is a printed wire board and the reference image corresponding to each local region of the printed wire board is a matrix of pixels of information arranged in N lines each one pixel in width. The size of each pixel and thus the width of each line correspond to the maximum expected pattern distortion within each local region. Where each corresponding reference image is a data base that is compared to a local region in successive lines and a reference image has N lines, the system repeats line N−1 of the reference image when the local region of the material is shorter in the first direction in the reference image and jumps from line N−1 to first line of the next local region of the reference image when the local region of the material is longer in the first direction. This procedure of dropping or repeating a line assures that the misalignment is not transferred to the next pair of images; the procedure is practicable since topical distortions in the printed wire board do not exceed the width of that line within each region.

Images are aligned in the second direction by shifting the image of each local region of the material and the corresponding reference image relative to each other. For alignment in the second direction the width of the scan in the second direction must be greater than the width in that direction of each local region; the images are aligned by selecting within the scan width the field of view in the second direction of information used to provide the image of each local region of the material to be inspected. Alignment in this direction is accomplished without dropping or repeating data.

Pattern inspection system 10, FIG. 1, utilizes comparator 12 to compare images of local regions of the material to be examined provided by camera assembly 14 with the corresponding reference image from reference image generator 16. Camera assembly 14 is moved along the Y-axis relative to the material to be inspected. Y-axis control circuit 18 monitors the relationship between the camera of camera assembly 14 and the material to be inspected; at the start of each local region, Y-axis control circuit 18 commands camera assembly 14 to commence scanning that region. X-axis control circuit 20 is responsive to Y-axis control circuit 18 and controls the rate at which image information for images along a second direction transverse to the first direction is fed to comparator 12 from camera assembly 14 and reference image generator 16. Errors detected are analyzed and displayed in display 22.

Preferably, each local region of the material to be examined is calibrated along both the X- and the Y-axes to the corresponding reference image for that local region. This information is fed as Y-calibration data 24 to Y-axis control circuit 18 and as X calibration data 26 to X-axis control circuit 20. Examples of alignment using this information are provided below.

Figure 2:
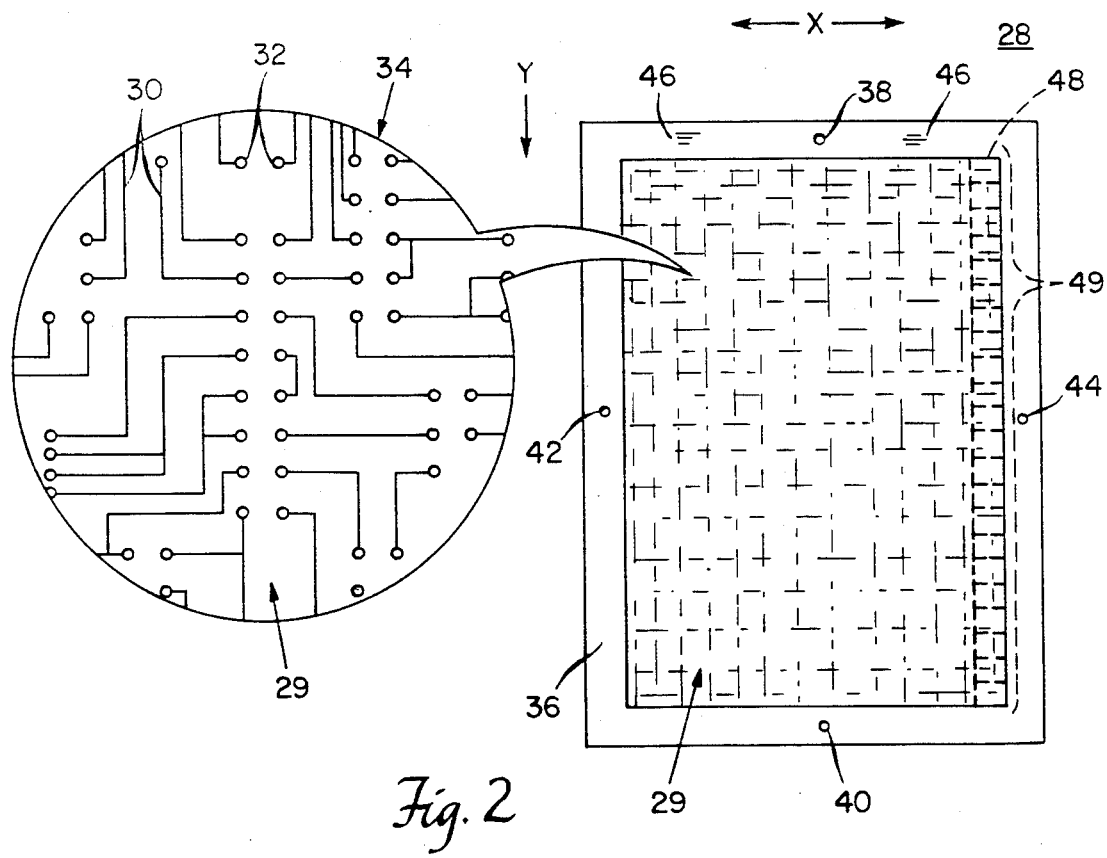
FIG. 2 is a schematic top plan view of a printed wire board to be inspected with an enlarged view of a portion of its lines and pads.

FIG. 2 illustrates a material to be inspected having a complex pattern disposed on it. Printed wire board 28 contains printed lines 30 and pads 32 as shown in balloon 34. Printed wire board 28 has one-inch border 36 with alignment holes 38, 40, 42 and 44 for receiving tool pins. Border 36 also contains registration marks 46 for permitting coarse optical alignment of the camera with board 28.

Typically, board 28 is eighteen inches in the direction indicated by X and twenty four inches in direction Y. Printed circuit 29 is typically sixteen inches by twenty two inches. For such a circuit, one-inch square areas are selected as local regions. Local region 48 is one of twenty two successive one-inch square local regions 49 along direction Y. As described below, each local region is inspected unit by unit wherein each unit—such as a pixel—is at least as large as the maximum expected pattern distortion over that local region; the size of the local region that is selected depends on the magnitude of the topical distortions within the pattern. Preferably, the size of the local region is small enough so that its scale does not change even though its actual X-Y location may shift relative to its expected X-Y location.

Figure 3:
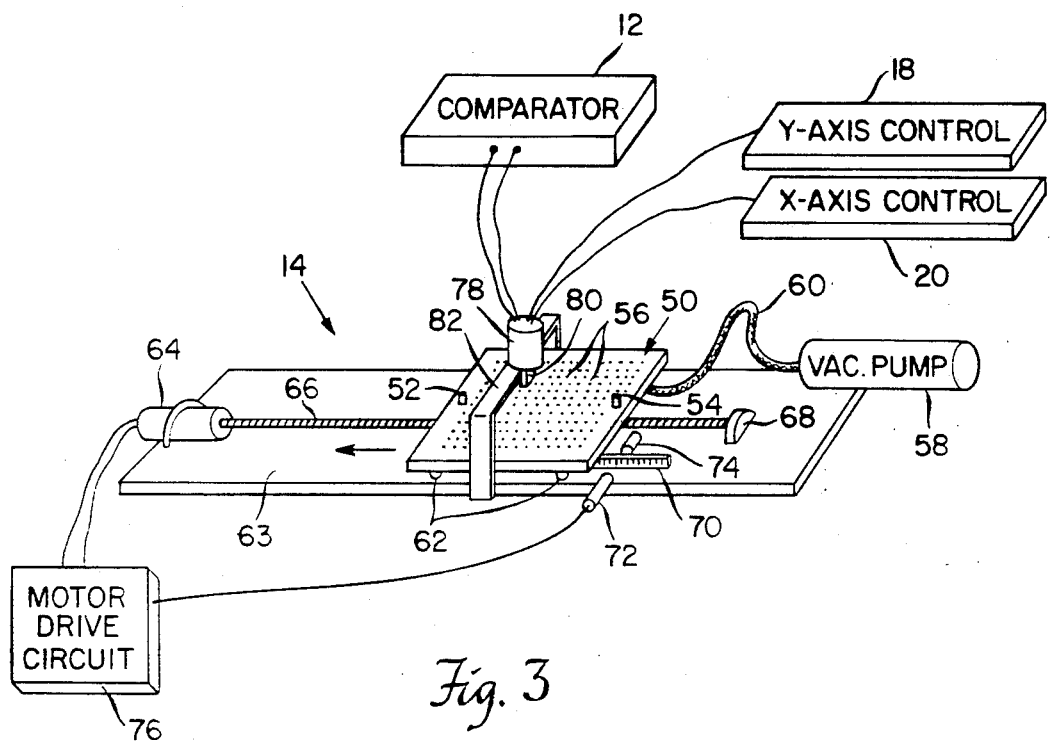
FIG. 3 is a schematic axonometric view of the camera assembly of FIG. 1.

Camera assembly 14, FIG. 3, has platen 50 for supporting printed wire board 28, FIG. 2. Tooling pins 52, 54 receive alignment holes 38, 40, respectively. Platen 50 also contains holes 56 for permitting vacuum pump 58 to apply a vacuum through vacuum hose 60 to printed wire board 28 when mounted on platen 50.

Platen 50 is mounted on wheels 62 which allow movement over table 63; DC motor 64 moves platen 50 toward and away from it using lead screw 66 which is mounted at its opposite end in bearing support 68. A stepper motor or linear motor can be substituted for DC motor 64.

Mounted beneath platen 50 is optically-clear glass scale 70; detector 72 monitors light transmitted through glass scale 70 by light source 74 to determine the position of platen 50. Alternatively, a magnetic scale and detectors can be used; a scale is not required when motor 64 is a stepper motor. Motor drive circuit 76 receives the output of detector 72 and controls the speed of DC motor 64 so that platen 50 is accelerated to and then maintained at a constant velocity while passing beneath camera 78. An acceptable constant velocity is 2.2 in/sec such that twenty-two local regions are scanned in 10 seconds.

Camera 78 with lens 80 is mounted upon fixed camera support 82. Camera 78 provides image output to comparator 12 at a rate determined by timing from Y-axis control 18 and X-axis control 20.

Figure 4:
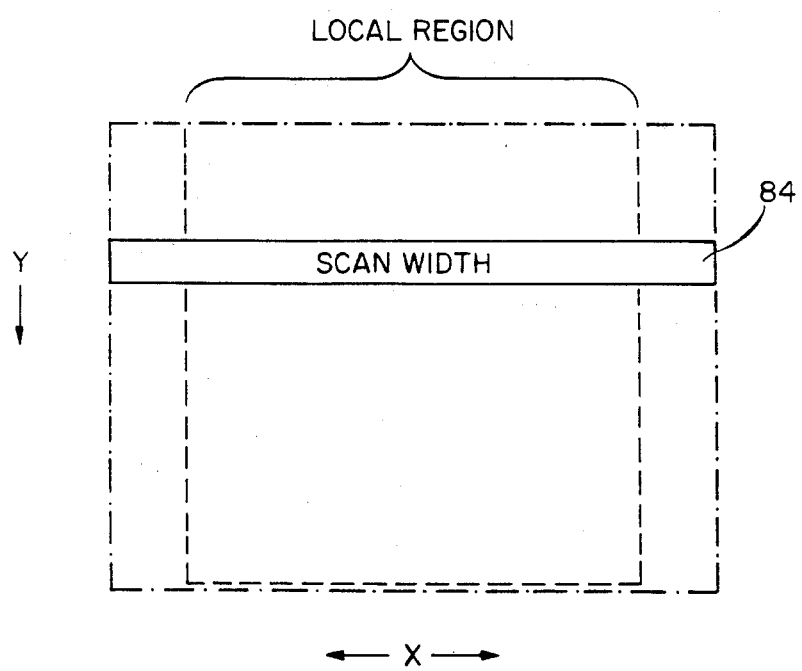
FIG. 4 is a schematic view of the dimensional relationship between a local region of the printed wire board of FIG. 2 and the scan width of the camera assembly of FIG. 3.

The field of view of camera 78 through lens 80 is selected according to the typical maximum amount of variation of the material to be inspected over a certain area. For inspecting a printed wire board, one-square inch viewing areas are desirable: the material rarely varies more than 0.0005 inch over that area. Camera 78 views each square inch area, or local region, as illustrated by scan width 84, FIG. 4. Camera 78 includes a linear array of 2048 detector elements, each element viewing a 0.0005 square inch area which is as large—in incremental value, not in total area—as the maximum expected pattern distortion in direction X or direction Y. The 2048 elements provide scan width 84 of 1.024 inches in width along direction X. Each detector element provides one pixel of image information. To view each one-inch square local region, 2000 of the 2048 elements are selected as the field of view to provide image information along direction X; alternatively, camera 78 can be physically shifted in direction X. Scan 84 is moved in direction Y relative to the printed wiring board for a distance of 2000 pixels, i.e., one inch. Sixteen cameras may be provided to view the entire width of a printed wiring board simultaneously, each camera viewing in succession twenty-two local regions.

Instead of moving the printed wire board in direction Y relative to a fixed camera, the camera can be movable. Also, the reference image can be obtained by optically scanning a reference or "golden" printed wire board region by region with a matching camera assembly as the board to be inspected is scanned. When the reference images are stored as data, the images can be separate and independent of each other or can be discrete segments of one reference data base that is the equivalent to one local region in width and a number of local regions in length. The systems described below utilize a region by region data base previously obtained by scanning a reference board.

Figure 5:
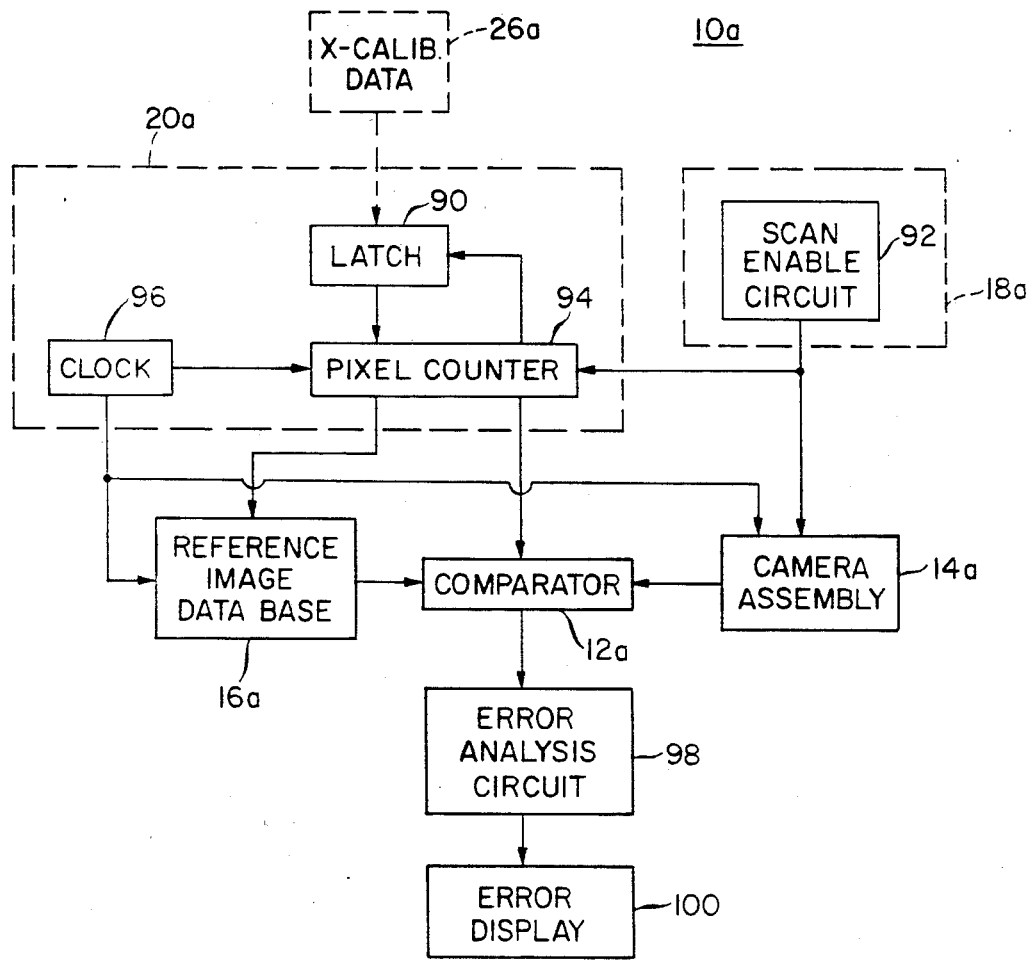
FIG. 5 is a schematic block diagram of an optical inspection system according to this invention which provides alignment along the X-axis of the material to be inspected with the reference image.

Optical inspection system 10a, FIG. 5, provides alignment in the X direction between reference image data base 16a and camera assembly 14a. Camera assembly 14a includes a charge-coupled device such as CD 143 available from Fairchild Camera and Instrument Corp., Palo Alto, Calif., and a threshold circuit to provide binary output. X-calibration data 26a contains an offset value which is the difference in position in the X direction between each local region of the printed wiring board to be inspected and the reference image for that local region. The offset for a given local region is provided to latch 90 of X-axis control circuit 20a. The 2048 detector elements of the charge-coupled device overlap each side of the local region in the X direction by 24 elements of 0.012 inch. Scan enable circuit 92 of Y-axis control circuit 18a indicates when a new line of scan begins by providing a start-of-line pulse to pixel counter 94 and camera assembly 14a.

The X-offset, a negative number between 0 and negative 47, is provided to pixel counter 94 which, after the start-of-line pulse is received from scan enable circuit 92, counts up to 0 at a rate set by clock 96. If there is no X-offset, counter 94 is loaded with the number −24. Once pixel counter 94 has counted up to zero, it enables reference image data base 16a to commence providing reference image information pixel by pixel to comparator 12a which begins comparing that reference information with the printed wire board information provided by camer assembly 14a. When pixel counter 94 counts up to 1999, the operation of reference data base 16a and comparator 12a is halted; additional image information from camera assembly 14a from the remaining detector elements is discarded. At count 2047, latch 90 again loads the X-offset for that region into pixel counter 94 to await the next start-of-line indication pulse from scan enable circuit 92.

Each time a pixel from camera assembly 14a does not match the corresponding pixel from reference data base 16a an error message is provided to error analysis circuit 98. Error analysis circuit 98 records the x, y coordinates of each discrepancy between the pixels and, for error events involving more than one pixel, provides as error boundaries for each error event minimum and maximum x values, minimum and maximum y values, and the total number of pixels of the error event. This information is displayed in error display 100.

Figure 6:
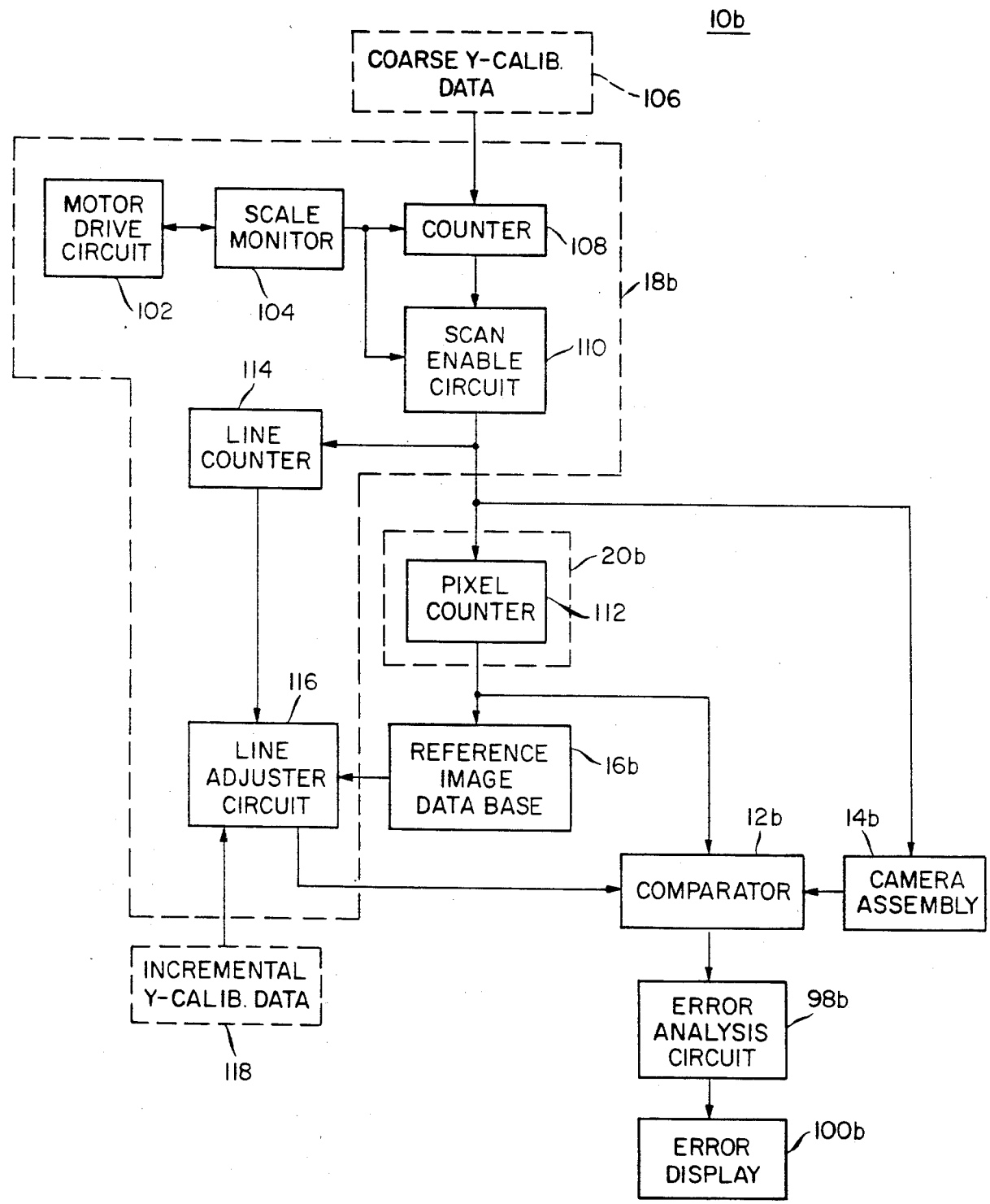
FIG. 6 is a schematic block diagram of an optical inspection system which provides alignment along the Y-axis.

Optical inspection system 10b, FIG. 6, provides alignment in the Y direction. Motor drive circuit 102 accelerates the platen carrying the printed wire board to be examined to achieve a predetermined constant velocity in the Y direction as indicated by scale monitor circuit 104. When two inches of platen travel is required to achieve constant velocity, coarse Y-calibration data 106 includes a count of 4000 plus a smaller offset amount determined from the alignment of the camera with the registration marks at the leading edge of the printed wire board; the small offset value depends on the board size and the location tolerances of pin alignment holes, for example. Counter 108 receives coarse data 108 as a negative number. Counter 108 counts up to zero at a count rate of once every 0.0005 inch as provided by scale monitor 104.

When the count reaches zero, counter 108 signals scan enable circuit 110 to provide a start-of-line scan pulse to pixel counter 112 of X-axis control circuit 20b, to camera assembly 14b, and to line counter 114. Counter 108 counts up to 44,000 for a 22-inch circuit pattern on a wire board.

Line counter 114 signals line adjuster circuit 116 when the last line of a local region approaches. Line adjuster circuit 116 receives incremental Y-calibration data 118 and alters lines of reference image information passing through it from reference image data base 16b as described below. Comparator 12b compares the reference data received through line adjuster circuit 116 with the image of the printed wire board from camera assembly 14b. The errors are analyzed by error analysis circuit 98b and displayed by error display 100b.

Figure 7:
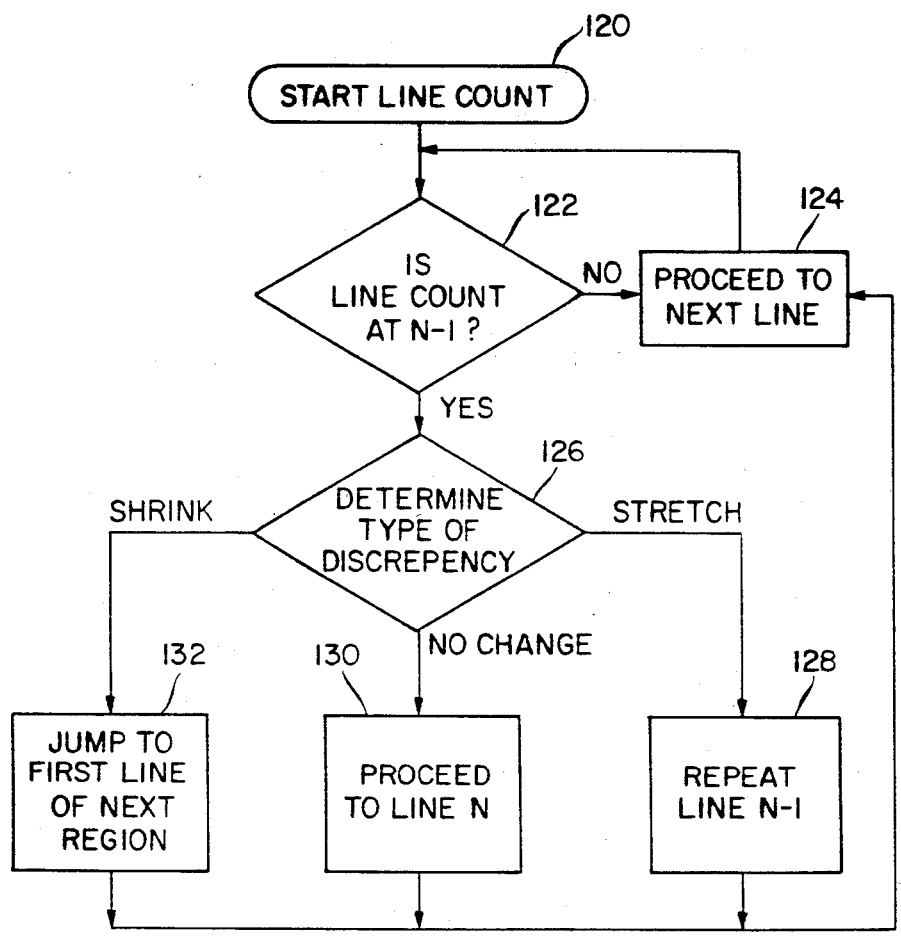
FIG. 7 is a flow chart representing the logic of the line adjuster circuit of FIG. 6.

The logic performed by line counter 114 and line adjuster circuit 116 is shown in FIG. 7. The line count begins at step 120 while a reference line is retrieved from the data base. The line count is examined at step 122 and, until the line count reaches N−1, the next line of reference image data is allowed, step 124, to proceed to the comparator. When the line count reaches N−1, the type of discrepancy between the reference data base and the board under inspection is determined at step 126; for example, the determination is provided by the incremental Y-calibration data input. When it is determined that the material in the next local region to be inspected has stretched relative to the reference image, line N−1 is repeated, step 128. Where there is no change in the next local region relative to the instant local region being viewed, the logic simply proceeds to line N, step 130. Where the material in the next region is shorter in dimension than the corresponding reference image, the adjuster circuit drops line N and jumps from line N−1 to the first line of the next region, step 132.

During operation of pattern inspection 10, FIG. 1, a reference printed wire board is placed on platen 50, FIG. 3, and scanned by camera 78 to develop a reference data base. This information is placed in reference image generator 16. The reference board is removed and a printed wire board to be inspected is then mounted on the platen. The board to be inspected is scanned by the camera so that each local region is compared in comparator 12 with the corresponding reference image from generator 16. The misalignment of each local region relative to its reference image is determined through error analysis to derive calibration data as described below. The platen is then repositioned and the board is scanned a second time to determine true errors due to actual pattern defects within each local region regardless of topical distortions.

Topical distortions are accommodated using separate alignment techniques for the X and Y directions. As the printed wire board approaches the camera during the error detection pass, the coarse Y-calibration data determines when comparison begins between the image of the local region provided by the camera and the corresponding reference image. The incremental Y-calibration data is first provided toward the end of the comparison between the first set of images to align in the Y direction the next set of images.

The local images and their corresponding reference images are aligned in the X direction using the X-calibration data to select the field of view of the camera as it scans each local region. The X-offset value for the local region being scanned is used repeatedly throughout the scan of that region as successive image lines are produced by the camera. The X-offset value is then updated for the succeeding local region.

Calibration data represents the misalignment between each local region and its corresponding reference image. In the two-pass procedure described above, a portion of the image, such as a pad of a line corner, within each local region is selected as a reference point; typically, 128 of the 2048 detector elements are monitored along 128 scan lines to encompass a pad. the pad location is then correlated with the matching image in the reference data base to determine the number of pixels of discrepancy in the X and Y direction. Alternatively, the center of a vertical line in the Y direction is selected for X-calibration and compared to the center of the line in the reference data base. The center of a horizontal line is used to determine the Y-calibration value. Since each local region is relatively small in area and is aligned independently, rotational displacements need not be considered.

The number of pixels of discrepancy is the offset value; the X-offset value for each local region is provided to latch 90 and pixel counter 94, FIG. 5, as X-calibration data 26a while the Y-offset value is provided to line adjuster circuit 116, FIG. 6, as Y-calibration data 118. Since local regions are scanned successivly and a topical distortion in one local region causes a misalignment for succeeding local regions, a running total of the offset values is maintained: the offset value of the preceding local region is incremented or decremented by one if a topical distortion affects the instant local region.

Alignment and inspection can be achieved in a single pass procedure by using the error values at a preselected line or pad in one local region as offset values in the next region. The first local region is aligned with the first reference image in the Y direction by using reference marks 46 or hole 38, FIG. 2. This Y-offset value is incremented, decremented, or left unchanged according to the Y-error value of a feature in the first local region. A running total for the Y-offset value is maintained as successive Y-error values are determined in turn from features in successive local regions.

The X-offset value can be determined in the same manner using a single pass procedure. The error values of a preceding region update the running offset total and serve as the offset values for the instant region being scanned. This procedure is acceptable but does not compensate for topical distortions in the instant region: the local region and its reference image can be misaligned without compensation in the X direction by one additional pixel and/or in the Y direction by one additional line. Misalignment by one pixel or one line is not critical, however, since individual features on the printed wire board encompass a number of pixels. Misalignment does become critical when it is continually accumulated without compensation for successive pairs of images over the entire length or width of the printed wire board: that is one of the problems that this invention overcomes.

Although specific features of the invention are shown in some drawings and not others this is for convenience only as each feature may be combined with any or all of the other features in accordance with the invention.

Other embodiments will occur to those skilled in the art and are within the following claims:

What is claimed is:

1. A system which inspects pattern-bearing material that is subject to topical distortions, comprising:
   means for scanning in a first direction a plurality of predefined local regions of a pattern to be inspected to provide an image of each local region, said means for scanning having a scan width, in a second direction, greater than the width in the second direction of each said local region;
   means for generating a reference image for each of said local regions;
   means for shifting the position of the image of each said local region and the position of its corresponding reference image relative to each other to align as a pair the images in the second direction;
   means for modifying in the first direction at least one of the dimension of the image of each said local region and the dimension of its corresponding reference image relative to each other to align as a pair the images in the first direction; and
   means for comparing each pair of aligned images to detect errors in the pattern independent of misalignment of and topical distortions of each said local region.

2. The inspection system of claim 1 in which said means for scanning includes camera means for producing the image of each said local region.

3. The inspection system of claim 2 in which said means for shifting includes means for selecting within the scan width the field of view of said camera means utilized to produce said image.

4. The inspection system of claim 3 in which said means for selecting includes means for determining for each said local region and its corresponding reference image the difference in position of said local region relative to the position of said reference image in the second direction.

5. The inspection system of claim 3 in which said camera means includes a plurality of photosensitive elements.

6. The inspection system of claim 5 in which said plurality of photosensitive elements includes a charge coupled device.

7. The inspection system of claim 1 in which said means for modifying includes means for representing for each said local region and its corresponding reference image the difference in dimension of said local region and the dimension of said reference image relative to each other in the first direction.

8. The inspection system of claim 7 in which said means for modifying further includes means for adjusting the dimension of said reference image in the first direction.

9. The inspection system of claim 8 in which said means for scanning provides the image of each said local region as a first set of successive portions and said means for generating generates its corresponding reference image as a second set of successive portions.

10. The inspection system of claim 9 in which said means for adjusting repeats a portion of said reference image when said local region is shorter in the first direction than said reference image and deletes a portion of said reference image when said local region is longer in the first direction.

11. The inspection system of claim 9 in which each said portion is a plurality of units and said means for comparing compares each local region unit to its corresponding reference image unit.

12. The inspection system of claim 11 in which each said unit is at least as large in dimension as the maximum expected topical distortion in the pattern of each said local region.

13. The inspection system of claim 8 in which said means for generating generates said reference image for each said local region as a set of successive lines.

14. The inspection system of claim 13 in which said means for adjusting, for a reference image having N lines, repeats line N−1 of said reference image when said local region is shorter in the first direction than said reference image and jumps from line N−1 to the first line of the next reference image when said local region is longer in the first direction.

15. The inspection system of claim 14 in which said reference images are arranged sequentially in the first direction.

16. The inspection system of claim 1 in which said means for generating generates digital reference images and includes memory means for storing the reference images in digital form.

17. The inspection system of claim 16 in which said means for scanning provides digital images of the local areas and the means for comparing includes digital comparison means.

18. The inspection system of claim 1 in which said pattern is disposed on a printed wire board.

19. The inspection system of claim 1 in which the second direction is transverse to the first direction along the plane of the pattern.

20. The inspection system of claim 1 in which said means for shifting and said means for modifying completely align each said local region with its corresponding reference image in the first and second directions.

21. The inspection system of claim 2 in which said means for scanning further includes movable platform means and means for securing the pattern to said platform means.

22. The inspection system of claim 21 further including means for coarsely aligning in the first direction said platform means and said camera means.

23. A system which inspects patternbearing material that is subject to topical distortions, comprising:
means for scanning in a first direction a plurality of predefined local regions of a pattern to be inspected to provide an image of each local region, said means for scanning having a scan width, in a second direction, greater than the width in the second direction of each said local region and having an adjustable field of view for producing the image of each said local region;
means for generating a reference image for each of said local regions;
means for shifting the position of the image of each said local region to align as a pair the images in the second direction, said means for shifting including means for selecting within the scan width of said means for scanning the field of view utilized to produce the image of each said local region; and
means for comparing each pair of aligned images to detect errors in the pattern independent of misalignment of and topical distortions of each said local region.

24. A system which inspects pattern-bearing material that is subject to topical distortions, comprising:
means for scanning in a first direction a plurality of predefined local regions of a pattern to be inspected to provide an image of each local region;
means for generating a reference image for each of said local regions;
means for modifying in the first direction at least one of the dimension of the image of each said local region and the dimension of its corresponding reference image relative to each other to align as a pair the images in the first direction; and
means for comparing each pair of aligned images to detect errors in the pattern independent of misalignment of and topical distortions of each said local region.

25. A method of inspecting pattern-bearing material that is subject to topical distortions, comprising:
defining a plurality of local regions in a pattern to be inspected;
scanning the pattern by passing in a first direction the local regions to provide an image of each local region, whereby the width of the scan in a second direction is greater than the width in the second direction of each local region;
establishing within the scan width a field of view for producing the image of each local region;
generating, for each local region, a reference image corresponding to that local region;
determining for each set of corresponding images the difference in position of the local region relative to the portion of its corresponding reference image in a second direction;
shifting the position of the image of each local region in the second direction to align the images in the second direction by adjusting the field of view utilized to produce the image of each local region; and comparing, for each local region, the aligned images to detect errors in the pattern independent of misalignment of and topical distortions of each said local region.

26. The method of claim 25 in which the step of determining includes initially scanning the pattern to view a portion of each region to resolve for that region any offset in the second direction.

27. The method of claim 26 in which the step of scanning to provide an image includes subsequently scanning each region by the field of view selected to compensate for the offset for that region.

28. A method of inspecting pattern-bearing material that varies nonuniformly, comprising:

defining a plurality of local regions in a pattern to be inspected;

scanning the pattern by passing in a first direction the local regions to provide an image of each local region;

generating, for each local region, a reference image corresponding to that local region;

representing for each set of corresponding images the difference in position of the local region relative to the position of its reference image in the first direction;

modifying in the first direction the dimension of the corresponding reference image relative to the image of that local region to align the images in the first direction; and comparing, for each local region, the aligned images to detect errors in the pattern independent of misalignment of and topical distortions of each said local region.

29. The method of claim 28 in which the step of representing includes initially scanning the pattern to view a portion of each region to resolve for that region any offset in the first direction.

30. The method of claim 29 in which the step of modifying includes altering the dimension of the corresponding reference image by the offset for that region.

31. The method of claim 28 in which the the dimension of the image of each local region is modified relative to the dimension of its corresponding reference image by repeating a portion of the reference image when the local region is shorter in the first direction than the reference image and deleting a portion of the reference image when the local region is longer in the first direction.

* * * * *